United States Patent [19]
Horiguchi

[11] Patent Number: 5,755,779
[45] Date of Patent: May 26, 1998

[54] BLOOD STREAM ADJUSTER

[76] Inventor: Sachio Horiguchi, 51-9, Okuikeminami-cho, Ashiya, 659, Japan

[21] Appl. No.: 741,747

[22] Filed: Nov. 5, 1996

[30] Foreign Application Priority Data

Dec. 7, 1995 [JP] Japan ................... 7-318837

[51] Int. Cl.$^6$ ........................... A61F 2/06; A61B 17/08
[52] U.S. Cl. ................................ 623/1; 606/158
[58] Field of Search ...................... 623/1, 11, 12; 606/157, 158

[56] References Cited

U.S. PATENT DOCUMENTS

| | | | |
|---|---|---|---|
| 4,562,597 | 1/1986 | Possis et al. | 623/1 |
| 4,957,508 | 9/1990 | Kaneko et al. | 623/1 |
| 4,986,831 | 1/1991 | King et al. | 623/1 |
| 5,084,064 | 1/1992 | Barak et al. | 623/1 |
| 5,139,515 | 8/1992 | Robicsek | 623/1 |

*Primary Examiner*—Debra S. Brittingham
*Attorney, Agent, or Firm*—Sixbey, Friedman, Leedom & Ferguson, PC; Gerald J. Ferguson, Jr.; Donald R. Studebaker

[57] ABSTRACT

A blood stream adjuster is arranged inside a blood vessel for bypass made of autologous blood vessel, artificial blood and so on when the blood vessel for bypass is transplanted between two blood vessels of the human body. The blood stream adjuster comprises a stricture portion which is located at its axis direction center part and has a smaller inside diameter in comparison with the inside diameters of axis direction both ends. The inside diameter of the stricture portion is set so that quantity, velocity or pressure of blood stream will be suitable for the blood vessel with which the side to receive blood stream in the blood vessel for bypass is anastomosed. Hereby, the occurrence of stricture and obstruction is restrained around the anastomotic portion between the blood vessel for bypass and its anastomotic blood vessel.

7 Claims, 3 Drawing Sheets

BLOOD STREAM ADJUSTER

BACKGROUND OF THE INVENTION

The present invention relates to a blood stream adjuster which is arranged inside a blood vessel for bypass made of autologous blood vessel, homogenous blood vessel, heterogenous blood vessel, artificial blood vessel and so on when the blood vessel for bypass is transplanted between two blood vessels at least of the human body.

The operation to use an artificial blood vessel, an autologous blood vessel, a homogenous blood vessel or a heterogenous blood vessel increases today in the field of surgical medical treatment. The artificial blood vessel is used on various transplantation operations for bypassing between two or further blood vessels of the human body, however, there is a problem regarding restricture and obstruction on the transplantation operation. Namely, when the operation for bypassing a coronary artery is performed, although a large saphenous vein or a internal chest artery is used as a blood vessel for bypass, restrictures and obstructions have occurred with time in many cases. Restrictures and obstructions occur similarly when an autologous vein is transplanted for obstruction arteriosclerosis. When an anastomosis is done between an artery and a vein in order to enforce blood dialysis and then expansion of the vein is planned, a inside membrane thickening occurs on the portion which various excessive hydrodynamic stresses affect. Referring to FIG. 5, when an artery 52 and a vein 53 are connected by an artificial blood vessel 51, thick inside membrane thickenings 54 occur on the anastomotic portion between the artificial blood vessel 51 and the vein 53, and an obstruction will occur.

Then, it is thought today that the cause of waking up such inside membrane thickening 54 and obstruction is related to adaptation reaction of the living body corresponding to hydrodynamic transition which a blood vessel receives. Namely, when shear stress or pressure persistently affects the wall of the blood vessel which is located at the side receiving blood stream at a high value exceeding the range that the blood vessel receives it usually, the inside membrane layer which is located between a blood vessel endothelium and a smooth musclelayer thickens, and a stricture portion occurs. Because shear stress becomes large further at the stricture portion, the inside membrane thickening progresses further, an obstruction occurs finally at the portion. In the statistical observation after operations of the transplantation blood vessel which this inventor did in the past, if velosity of blood stream, pressure or shear stress had become larger than the proper value corresponding to an anastomotic blood vessel around the anastomotic portion between a transplantation blood vessel and the anastomotic blood vessel, internal membrane thickening, endothelial shrink and change of ulcer were seen.

Consequently, in order to restrain the obstruction, it is thought to adjust the blood stream to flow in a blood vessel for bypass when it is transplanted. However, on the method to adjust the blood stream by pressing the blood vessel for bypass from its exterior in order to make a stricture portion, the inside membrane of the stricture portion thickens, then an obstruction occurs. It is also thought to adjust the blood stream by forming an artificial blood vessel itself into tapering form when it is used as a blood vessel for bypass (reference of Japanese Patent Publication No. 6-14941). However, if the caliber of the artificial blood vessel is small, its suture gets difficult and inaccurate. It is not easy to set the ratio of a small caliber to a large caliber properly, and it is actually impossible to set the length and the ratio of caliber of an artificial blood vessel respectively properly.

SUMMARY OF THE INVENTION

It is an object of the present invention to provide a blood stream adjuster to restrain the occurrence of stricture and obstruction around the anastomotic portion between a blood vessel for bypass and its anastomotic blood vessel by adjusting the blood stream in the blood vessel for bybass appropriately when it is transplanted.

For this object, the present invention presupposes that a blood stream adjuster is arranged inside a blood vessel for bypass when the blood vessel for bypass is transplanted between two blood vessels at least of the human body. The blood stream adjuster comprises a stricture portion which is located at its axis direction center part and has a smaller inside diameter in comparison with the inside diameters of axis direction both ends, the inside diameter of the stricture portion is set so that quantity, velocity or pressure of blood stream will be suitable for the blood vessel with which the side to receive blood stream in the blood vessel for bypass is anastomosed. Then, after such a transplantation, the blood stream in the blood vessel for bypass is adjusted at the stricture portion of the blood stream adjuster, and quantity, velocity or pressure of blood stream is suitable for the blood vessel. Therefore, the occurrence of stricture and obstruction is restrained around the anastomotic portion between the blood vessel for bypass and its anastomotic blood vessel. Moreover, it is not necessary to make the caliber of the blood vessel for bypass small. The suture gets easy, the blood stream adjustment also gets comparatively easy.

BRIEF DESCRIPTION OF THE DRAWINGS

The above and other objects and advantages of the present invention will appear more from reading of the following detailed description and appended drawings, in which.

DETAILED DESCRIPTION OF THE PREFERRED EMBODIMENTS

Figure 1:
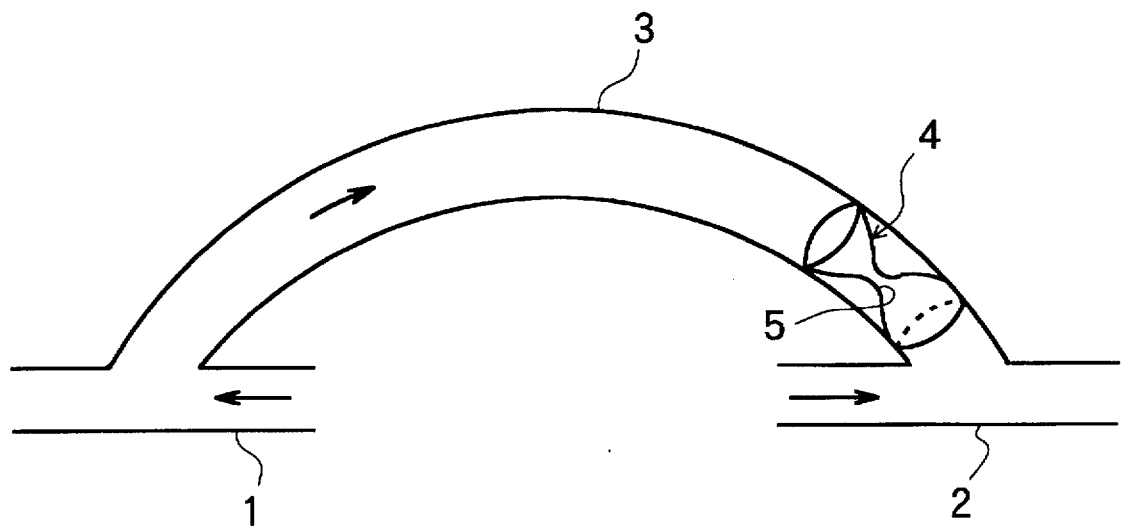
FIG. 1 is a schematic illustration showing the state that a blood vessel for bypass having a blood stream adjuster relating to the first embodiment of the present invention is transplanted between an artery and a vein.

Referring now to FIG. 1, reference numeral 1 is an artery such as brachial artery of the human body, reference numeral 2 is a vein such as axillary vein of the human body, and reference numeral 3 is a blood vessel for bypass transplanted between the artery 1 and the vein 2 in order to return blood at the vein 2 from the artery 1. The blood vessel 3 is made of an artificial blood vessel. A blood stream adjuster 4 relating to the first embodiment of the present invention is arranged inside one end part (the near side to the vein 2) of the blood vessel 3.

Figure 2:
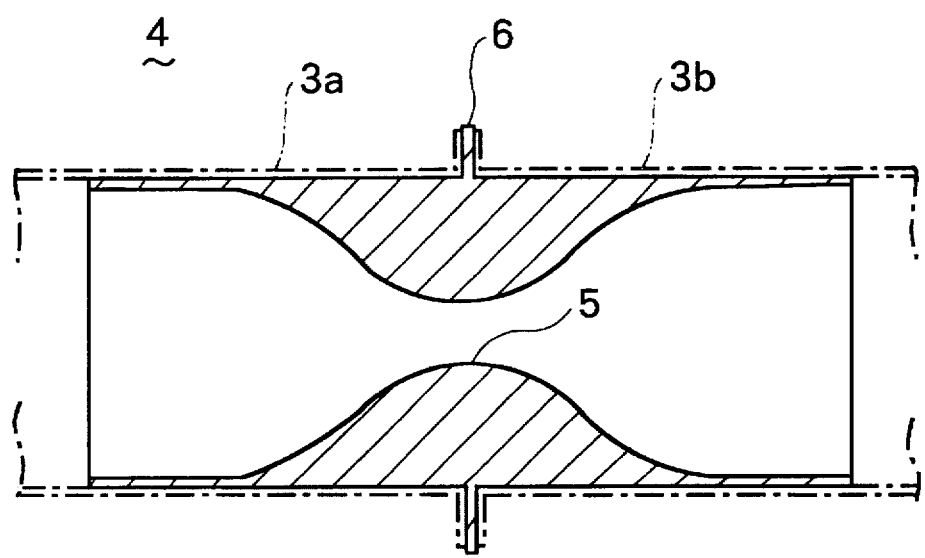
FIG. 2 is a vertical cross section of the above blood stream adjuster.

The blood stream adjuster 4, which is shown in detail in FIG. 2, is about cylindrical shape as a whole and comprises a stricture portion 5 which is located at its axis direction center part and has a smaller inside diameter in comparison with the inside diameters of axis direction both ends. The inside diameter of the stricture portion 5 is set so that quantity or velocity of blood stream will be suitable for the vein 2 with which the downstream side to receive blood stream in the blood vessel 3 is anastomosed. The quantity or the velocity of blood stream to be suitable for the vein 2 is the range that wall shear stress to affect the wall of the vein 2 by it becomes within 1.5 to 15 dyne/cm$^2$ (0.15 to 1.5 Pa). By the way, the quantity or the velocity of blood stream to be suitable for the artery 1 is the range that wall shear stress to affect the wall of the artery 1 by it becomes within 10 to 50 dyne /cm$^2$ (1 to 5 Pa).

Hydrodynamically considering, if quantity of blood stream increases on the condition that inside diameter never change, velocity of blood stream increases, and also wall shear stress increases simultaneously. The average velocity of blood stream is in inverse proportion to the square of inside diameter from its calculation expression "quantity of blood stream/transverse sectional inside area ($\pi r^2$)", and wall shear stress is in inverse proportion to the cube of inside diameter from the formula of Hagen Poiseuill "stickiness× 4×quantity of blood stream/$\pi r^3$", which is its calculation expression. Consequently, when the artificial blood vessel 3 is transplanted between the artery 1 and the vein 2, if the effective caliber (inside diameter) of the artificial blood vessel 3 is 7 mm and the average velocity of blood stream is in inverse proportion to the square of inside diameter, the inside diameter of the stricture portion 5 is set at 2.2 mm. If the effective caliber of the artificial blood vessel 3 is 5.4 mm and wall shear stress is in inverse proportion to the cube of inside diameter, the inside diameter of the stricture portion 5 is set at 2.0 mm.

The blood stream adjuster 4 has a ringed collar portion 6 for suture at its axis direction center part. The ringed collar portion 6 is molded in one body with the outside face of the blood stream adjuster 4 and projects into the outside. Then, when the blood stream adjuster 4 is arranged inside the blood vessel 3, the blood vessel 3 is cut in two first. Continue, the blood stream adjuster 4 is covered with the two cutting blood vessels 3a and 3b respectively from its both ends, the cutting blood vessels 3a and 3b is put each other at the state clipping the ringed collar portion 6. Thereafter, these three portions 3a, 3b and 6 is sutured together.

Although it is good to use any of monomaterial and compound material of metal, ceramic, plastics, fiber, glass, etc. and material applying coating on these as material of the blood stream adjuster 4, the material of the blood stream adjuster 4, which is similar to it of the artificial blood vessel 3, is necessary to satisfy the following conditions:

(a) Living body adaptation is well;
(b) There are not virulence and resolution;
(c) There is X-ray induction, and then it is able to confirm the position and the shape;
(d) It is desirable to be non-magnetic material; and
(e) There is tolerance of heat and body fluid, and it is hard to cause deformation.

Explaining the action and effect of the above first embodiment hereinafter, when blood flows from the artery 1 to the vein 2 through the blood vessel 3 after the transplantation of the blood vessel 3, the blood stream in the blood vessel 3 is adjusted by the stricture portion 5 of the blood stream adjuster 4, and then quantity or velocity of the blood stream is suitable for the vein 2. Concretely, when the blood stream in the blood vessel 3 flows into the vein 2, wall shear stress on the wall of the vein 2, which is occured by the blood stream, becomes within the range of 1.5 to 15 dyne/cm$^2$ (0.15 to 1.5 Pa) which is similar to the range that a vein of the human body receives wall shear stress usually. Thereby, it is effectively restrained that restricture and obstruction occur around the anastomotic portion between the blood vessel 3 and the vein 2, and the elapse after a transplantation operation gets well.

Moreover, because it is not necessary to set the caliber of the blood vessel 3 itself small for the adjustment of blood stream, it is possible to suture the blood vessel 3 the vein 2 and the artery 1 easily. It is also possible to adjust blood stream comparatively easily at the stricture portion 5. Because the blood stream adjuster 4 has the collar portion 6 at its outside face, it is possible to fix the blood stream adjuster 4 to the blood vessel 3 certainly by suturing the both at the collar portion 6 when the blood stream adjuster 4 is arranged inside the blood vessel 3 before the transplantation operation.

By the way, although it is adopted in the first embodiment to adjust the blood stream in the blood vessel 3 by the stricture portion 5 of the blood stream adjuster 4 arranged inside the blood vessel 3 and adapt its velocity or velocity to the vein 2, the present invention includes adjusting pressure of blood stream instead of its quantity or velocity within the range of pressure affecting the wall of the vein 2 usually. It is possible to restrain the occurrence of stricture and obstruction around the anastomotic portion between the blood vessel 3 and the vein 2 also in this case.

It is possible to use the blood stream adjuster 4 of the present invention not only at the time to transplant a blood vessel for bypass between an artery and a vein like the above first embodiment but also at the time to transplant a blood vessel for bypass between a vein and other vein or between an artery and other artery. The present invention includes using not only an artificial blood vessel like the above first embodiment but also an autologous blood vessel, a homogenous blood vessel or a heterogenous blood vessel as the blood vessel 3 for bypass. Further, the present invention includes molding a blood stream adjuster in one body with another apparatus to be arranged inside an artificial blood vessel for bypass, for example the apparatus (trade name-hemasito) in order to take blood out the human body for autodialysis and so on.

Figure 3:
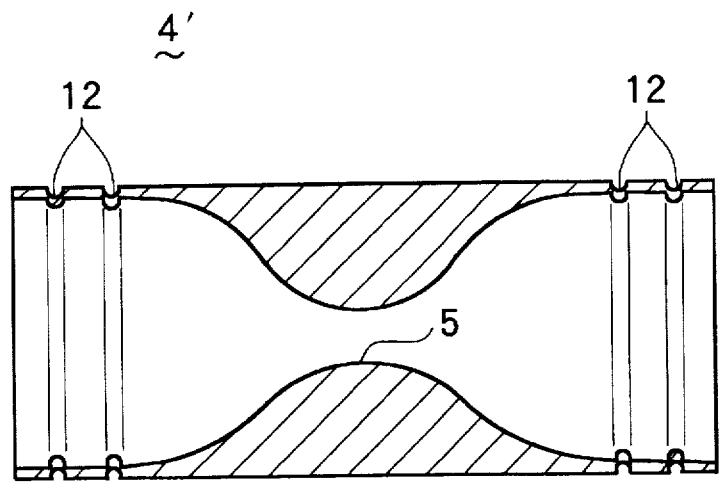
FIG. 3 is a view equivalent to FIG. 2 showing the second embodiment of the present invention.

FIG. 3 shows a blood stream adjuster 4' relating to the second embodiment of the present invention. The blood stream adjuster 4' has two ringed ditches 12 respectively at the outside face of its both end parts, and is fixed to a blood vessel for bypass by tying at each ringed ditch 12 on the blood vessel after the blood stream adjuster 4' has been inserted inside the blood vessel. By the way, other construction of the blood stream adjuster 4' is similar to it of the blood stream adjuster 4 relating to the first embodiment, like element is given like reference numeral 5.

Figure 4:
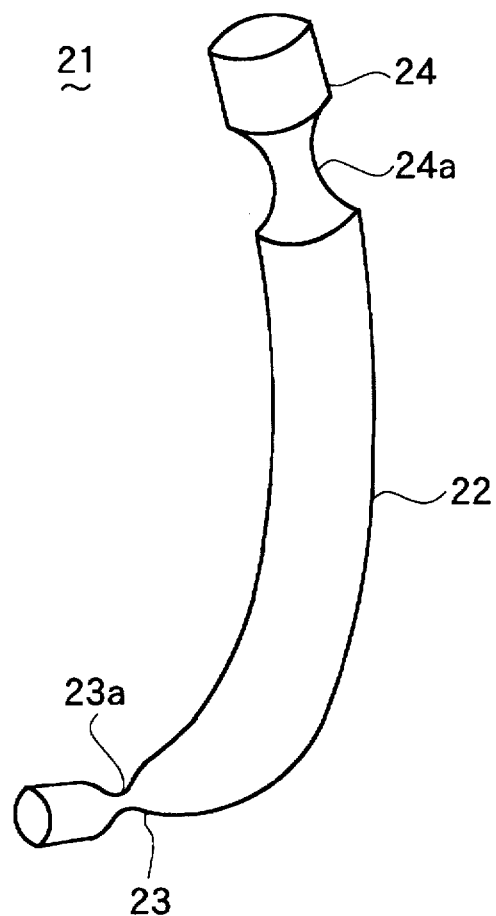
FIG. 4 is a schematic illustration showing an artificial blood vessel for bypass relating to the third embodiment of the present invention.
Figure 5:
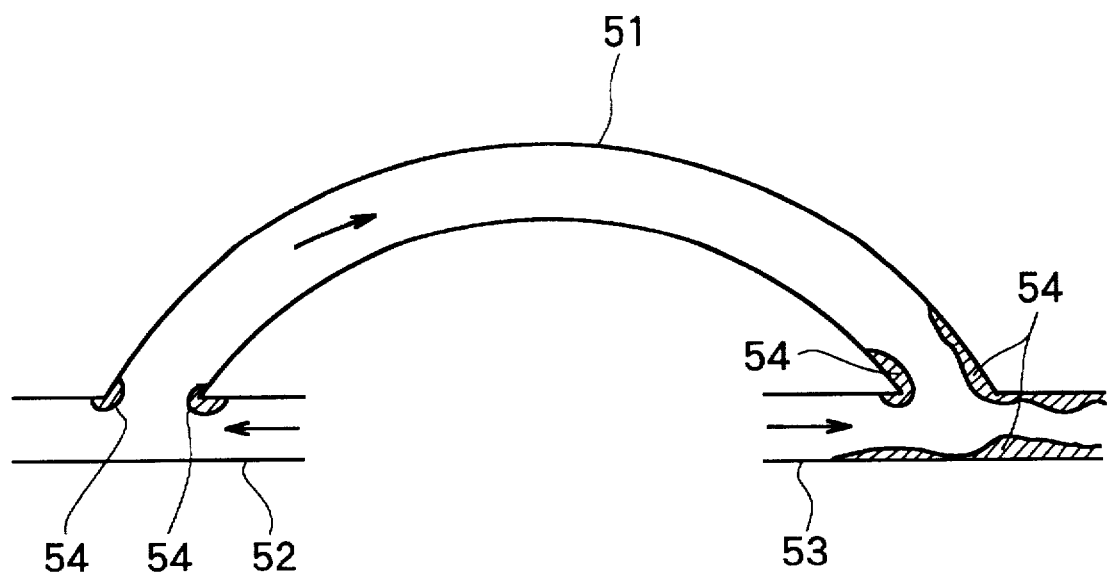
FIG. 5 is a schematic illustration showing the state that inside membrane thickenings have occurred at an anastomotic portion after the transplantation of an artificial blood vessel.

FIG. 4 shows an artificial blood vessel 21 for bypass relating to the third embodiment of the present invention. The artificial blood vessel 21 will be transplanted in order to connect two blood vessels of the human body. A blood stream adjuster 23 is arranged inside one end part (the downstream side) of the main body 22 of the artificial blood vessel 21 by insertion or molding in one body, another blood stream adjuster 24 is arranged inside the other end part (the upper stream side) of the main body 22 in a similar way.

The blood stream adjuster 23 comprises a stricture portion 23a which is located at its axis direction center part and has a smaller inside diameter in comparison with the inside diameters of axis direction both ends. The inside diameter of the stricture portion 23a, which is similar to it of the stricture portion 5 of the blood stream adjuster 4 relating to the above first embodiment, is set so that quantity, velocity or pressure of blood stream to flow at its downstream side will be suitable for a blood veseel with which the downstream side to receive blood stream in the main body 22 is anastomosed. Hereby, it is possible to restrain the occurrence of stricture and obstruction around the anastomotic portion between the artificial blood vessel 21 and its anastomotic blood vessel.

On the other hand, the inside diameter of the main body 22 is set at a larger value in comparison with the standard inside diameter which is necessary size in order that blood will flow in it. The blood stream adjuster 24 has a stricture portion 24a in order to adjust the quantity of blood stream in the main body 22. Hereby, it is possible to adjust the quantity of blood stream in the main part 22 by the stricture portion 24a of the blood stream adjuster 24 and cut down pressure loss at the main body 22 because its inside diameter is large. Consequently, it is valid to use the artificial blood vessel 21 for bypass especially at the time to transplant in order to connect two blood vessels which are located mutually comparatively apart in the human body.

What is claimed is:

1. A unitary blood stream adjuster positioned inside a blood vessel for bypass when the blood vessel for bypass is transplanted between two blood vessels at least of the human body, the blood stream adjuster comprising a stricture portion located at a center region of the adjuster having a predetermined inside diameter, said predetermined inside diameter being smaller than inside diameters of end regions of the adjuster, the predetermined inside diameter of the stricture portion being set so that a physical quantity selected from a group consisting of quantity, velocity and pressure of a blood stream will be suitable for the blood vessel with which the side to receive the blood stream in the blood vessel for bypass is anastomosed.

2. A blood stream adjuster as claimed in claim 1, in which the quantity or the velocity of the blood stream to be suitable for the blood vessel is the range that shear stress to affect a wall of the blood vessel by it becomes within 10 to 50 dyne/cm$^2$ (1 to 5 Pa) if the blood vessel is an artery, 1.5 to 15 dyne/cm$^2$ (0.15 to 1.5 Pa) if the blood vessel is a vein.

3. A blood stream adjuster as claimed in claim 1, in which the blood stream adjuster has a ringed collar portion to suture with the blood bessel for bypass.

4. A blood stream adjuster as claimed in claim 1, in which the blood vessel for bypass is made of an artificial blood vessel.

5. A blood stream adjuster as claimed in claim 4, in which the blood stream adjuster is molded in one body with another apparatus to be arranged inside the artificial blood vessel.

6. An artificial blood vessel for bypass to be transplanted in order to connect two blood vessels of the human body, in which the artificial blood vessel for bypass comprises a main body and a unitary blood stream adjuster arranged inside one side of the main body, the blood stream adjuster comprising a stricture portion located at a center region of said adjuster having a predetermined inside diameter, said predetermined inside diameter being smaller than inside diameters of end regions of said adjuster, the predetermined inside diameter of the stricture portion being set so that a physical quantity selected from a group consisting of quantity, velocity and pressure of blood stream will be suitable for the blood vessel with which the side to receive the blood stream in the main body is anastomosed.

7. An artificial blood vessel for bypass as claimed in claim 6, in which the inside diameter of the main body is set at a larger value in comparison with an inside diameter which is of a necessary size in order that blood will flow in it, the artificial blood vessel for bypass comprises another blood stream adjuster arranged inside the other side of the main body further, the blood stream adjuster has a stricture portion in order to adjust the quantity of blood stream in the main body.

* * * * *